United States Patent [19]
Merrill et al.

[11] Patent Number: 5,830,986
[45] Date of Patent: Nov. 3, 1998

[54] METHODS FOR THE SYNTHESIS OF FUNCTIONALIZABLE POLY(ETHYLENE OXIDE) STAR MACROMOLECULES

[75] Inventors: Edward W. Merrill, Belmont; Diane Rintzler Yen, Arlington; Ambuj Sagar, Cambridge, all of Mass.

[73] Assignee: Massachusetts Institute of Technology, Cambridge, Mass.

[21] Appl. No.: 740,155

[22] Filed: Oct. 28, 1996

[51] Int. Cl.⁶ .................................................. C08G 69/26
[52] U.S. Cl. ........................ 528/332; 525/451; 528/363; 528/425; 528/494
[58] Field of Search .................................. 528/425, 494, 528/332, 363; 525/451

[56] References Cited

U.S. PATENT DOCUMENTS

| | | |
|---|---|---|
| 4,487,808 | 12/1984 | Lambert . |
| 4,568,737 | 2/1986 | Tomalia et al. ......................... 528/332 |
| 5,171,264 | 12/1992 | Merrill . |
| 5,275,838 | 1/1994 | Merrill . |
| 5,276,110 | 1/1994 | Zhou et al. . |
| 5,290,548 | 3/1994 | Goldberg et al. . |
| 5,308,428 | 5/1994 | Simpson et al. . |
| 5,401,327 | 3/1995 | Ellis et al. . |
| 5,461,116 | 10/1995 | Hoxmeier et al. . |
| 5,509,899 | 4/1996 | Fan et al. . |

FOREIGN PATENT DOCUMENTS

| | | |
|---|---|---|
| 0093094A1 | 11/1983 | European Pat. Off. . |
| 0323341A2 | 7/1989 | European Pat. Off. . |
| 2665902 | 2/1992 | France . |
| 1032505 | 6/1966 | United Kingdom . |
| WO 86/02087 | 4/1986 | WIPO . |
| WO 90/00343 | 1/1990 | WIPO . |
| WO 91/12886 | 9/1991 | WIPO . |
| WO 93/21259 | 10/1993 | WIPO . |
| WO 95/18840 | 7/1995 | WIPO . |
| WO 96/09086 | 3/1996 | WIPO . |
| WO 96/14887 | 5/1996 | WIPO . |

OTHER PUBLICATIONS

Tomalia, et al., "Dendritic Macromolecules: Synthesis of Starburst Dendrimers," *Macromolecules*, 19:2466–2468 (1986).
Voit and Turner, "Dendritische und Hyperbranched Polymere," *Die Angewandte Makromolekulare Chemie*, 223:13–27 (1994) (German with English abstract).
Aharoni, et al., "Size and Solution Properties of Globular tert–Butyloxycarbonyl–poly(α,ε–L–lysine)", *Macromolecules*, 15:1093–1098 (1982).
Aldrich Catalog, Aldrich Chemical Co., Inc., p. 1215 (1996).
Bayer & Stadler, "Synthesis And Properties Of Amphiphilic Dumbbell–Shaped Grafted Block Copolymers, 1", *Macromol. Chem. Phys.*, 195:2709–2722 (1994).
Fried, Polymer Science and Technology, Prentice Hall Ptr, Upper Saddle River, New Jersey, 13 (1995).
Gnanou, et al., "Synthesis Of Star–Shaped Poly(ethylene oxide)" *Makromol. Chemie*, 189:2885–2892 (1988).
Greene & Wuts, "Protective Groups in Organic Synthesis", Second Edition, John Wiley and Sons, Inc., New York, 1991.
Haggin, et al., "Dendrimers Engineered to Provide New Catalysts", *C&EN*, pp. 26–27, Feb. 6, 1995.
Harris, "Laboratory Synthesis Of Polyethylene Glycol Derivatives", *J. Macromolecular Sci. Reviews in Macro. Chem. Phys.*, C25(3):325–373 (1985).
Harris, Poly(ethylene glycol) Chemistry: Biotechnical and Biomedical Applications; Plenum Press: New York, 1992.
Jansen, et al., *Polym. Mater. Sci. Eng.*, 73:123–4 (1995).
Lutz & Rempp, "New Developments in Star Polymer Synthesis. Star–Shaped Polystyrenes and Star–Block Copolymers", *Makromol. Chem.*, 189:1051–1060 (1988).
March, "Advanced Organic Chemistry, Reactions, Mechanisms, and Structure", John Wiley & Sons, New York, 1992.
Merrill, et al., "Transformation Of Polymer Surfaces By Covalent Grafting Of Poly(ethylene Oxide) Star Molecules For Biomedical Applications", Mit. Chemical Eng., 1–2.
Merrill, "Poly(ethylene oxide) Star Molecules: Synthesis characterization, And Applications in Medicine And Biology", *J. Biomat. Sci. Polymer Edn.*, 5(1/2):1–11 (1993).
O'Sullivan, "Dendrimers Nearing Availability for Commercial Evaluation", *C&EN*, pp. 20 Aug. 16, 1993.
Teyssic & Jerome, "Naphthalene Chemistry: II: A Novel Route For The Synthesis Of Well Defined Star Block Copolymers Displaying An A(B) Architecture From Hydrocarbon Monomers (A) And Ethylene Oxide (B)", Polymer Preprints, 20(2):344–348 (1979).
Van Genderen & Meijer (1st International Symposium on Polymer Therapeutics, Jan. 10–12, 1996, University of Alabama School of Pharmacy).
Ward, et al., "Surface Modification", Encyclopedia of Polumer Science and Engineering, 2d Edition, 674–689 (1985).
Zhou & Roovers, "Synthesis Of Novel Carbosilane Dendritic Macromolecules", 26:963–968 (1993).

*Primary Examiner*—John M. Cooney, Jr.
*Attorney, Agent, or Firm*—Arnall Golden & Gregory, LLP

[57] ABSTRACT

Methods are provided for the synthesis of poly(ethylene oxide) ("PEO") star macromolecules including functionalizable groups. In one embodiment, a core molecule including a plurality of dendritic branches or having a comb structure, and including a plurality of accessible reactive groups is reacted with functionalizable poly(ethylene oxide) ("PEO") molecules. The functionalizable poly(ethylene oxide) molecules include a reactive group capable of reacting with the reactive group on the core molecule, and a functionalizable group capable of being chemically modified, which optionally is protected. In the reaction, the PEO molecules are covalently attached to the core molecule, to form a PEO star macromolecule with terminal functionalizable groups. Preferably, the functionalizable PEO is a heterofunctional linear PEO which includes the reactive group at one terminus and the functionalizable group at the other terminus. The functionalizable groups on the PEO molecules then may be deprotected if necessary, and then further derivatized, for example, by the attachment of a biologically active molecule or polymer thereof.

42 Claims, 5 Drawing Sheets

| PEO Type | MPEO Note a | Dendrimer functionality (fd) Note b | Dendrimer Mol Weight (Md) Note b | Star Mn expected Note c | Star Mn found Note d | pdi Note d | Star functionality fs Note e | Fraction of dendrimer functions used fs/fd |
|---|---|---|---|---|---|---|---|---|
| MeO-PEO-CH$_2$CH$_2$CONHS | 5000 | 16 | 3206 | 83256 | 88700 | 1.09 | 17 | 1.06 |
| MeO-PEO-CH$_2$CH$_2$CONHS | 5000 | 32 | 6909 | 166909 | 161000 | 1.06 | 31 | 0.97 |
| MeO-PEO-CH$_2$CH$_2$CONHS | 5000 | 64 | 14215 | 334215 | 268000 | 1.01 | 51 | 0.80 |
| MeO-PEO-CH$_2$CH$_2$CONHS | 5000 | 128 | 28000 | 668000 | 496000 | 1.06 | 94 | 0.73 |
| MeO-PEO-CH$_2$CH$_2$CONHS | 5000 | 256 | 50845 | 1336000 | 778000 | 1.03 | 144 | 0.56 |
| HO-PEO-CH$_2$CH$_2$CONHS | 4000 | 16 | 3206 | 67260 | 76600 | 1.15 | 18 | 1.38 |
| HO-PEO-CH$_2$CH$_2$CONHS | 4000 | 32 | 6909 | 134909 | 121000 | 1.2 | 29 | 1.06 |
| HO-PEO-CH$_2$CH$_2$CONHS | 4000 | 64 | 14215 | 270215 | 235000 | 1.24 | 56 | 1.03 |
| HO-PEO-CH$_2$CH$_2$CONHS | 4000 | 128 | 28000 | 540000 | 416000 | 1.05 | 97 | 0.90 |
| HO-PEO-CH$_2$CH$_2$CONHS | 4000 | 256 | 50845 | 1080000 | 498000 | 1.04 | 112 | 0.52 |
| t-boc-PEO-CH$_2$CH$_2$CONHS | 3400 | 64 | 14215 | 231815 | 177000 | 1.05 | 48 | 0.81 |

Notes:
(a) MPEO, MOLECULAR WEIGHT OF THE PEO, g-mol-1, AS REPORTED BY SUPPLIER, SHEARWATER POLYMERS, INC.
(b) NUMBER OF AMINO FUNCTIONS, fd, AND MOLECULAR WEIGHT, Md, OF THE DENDRIMER AS REPORTED BY SUPPLIER, ALDRICH CHEMICAL CO. AS SELLING AGENT, OR DENDRITECH, INC.
(c) CALCULATE BY THE FORMULA: $Mn, ex = MPEO \cdot fd + Md$, WHERE $Mn, ex$ = EXPECTED MOLECULAR WEIGHT OF THE PEO STAR MACROMOLECULE
(d) DETERMINED BY GPC-LS, $Mn, fd$ IS THE EXPERIMENTALLY DETERMINED MOLECULAR WEIGHT OF THE PEO STAR MACROMOLECULE BY GPC-LS THE WEIGHT AVERAGE MOLECULAR WEIGHT MW IS ALSO DETERMINED, AND Mw/Mn IS THE POLYDISPERSITY INDEX pdi
(e) APPARENT STAR FUNCTIONALITY, fs, AS CALCULATED BY THE FORMULA: $fs = (Mn, fd - Md)/MPEO$

METHODS FOR THE SYNTHESIS OF FUNCTIONALIZABLE POLY(ETHYLENE OXIDE) STAR MACROMOLECULES

The present invention is generally in the area of the synthesis of poly(ethylene oxide) ("PEO") star molecules including reactive functionalizable groups.

BACKGROUND OF THE INVENTION

Linear poly(ethylene oxide) (PEO) has been of interest for a long time due to its many unusual physical chemistry properties, including its ability to repel other polymers in aqueous solution, which leads to protein repulsion by both PEO in solution and by surfaces covered by immobilized PEO. Harris, J. M., *Poly(ethylene glycol) Chemistry: Biotechnical and Biomedical Applications*; Plenum Press: New York, 1992. Recently, there has been increasing interest in PEO star molecules. PEO star molecules are a form of a branched polymer which include PEO "arms" attached to a central core. The core molecular weight is usually a small fraction (<6%) of the total molecular weight of the star molecule. PEO star molecules have been immobilized on surfaces in the form of hydrogel layers which are biocompatible and non-thrombogenic. U.S. Pat. Nos. 5,275,838 and 5,171,264 to Merrill, the disclosures of which are incorporated herein by reference.

PEO star molecules have been prepared by a living anionic polymerization reaction using a divinylbenzene ("DVB") core. Lutz and Rempp, *Makromol. Chem.*, 189:1051 (1988); Gnanou et al., *Makromol. Chemie*, 189:2885–2892 (1988); and Merrill, *J. Biomater. Sci. Polymer Edn.*, 5:1–11 (1993). The cores are synthesized first, followed by growing PEO arms outward from the core using ethylene oxide. This method produces a sample of PEO star molecules which are very polydisperse, possibly due to an uneven growth rate of the cores leading to star molecules with varying functionalities. The PEO star molecules also have been found to be difficult to fractionate using conventional techniques such as ultrafiltration or classical temperature manipulation.

Van Genderen and Meijer (1st International Symposium on Polymer Therapeutics, Jan. 10–12, 1996, University of Alabama School of Pharmacy) reported the attachment of methoxy terminated oligo(ethylene oxides) to a fifth generation poly(propylene imine) dendrimer. The resulting starlike molecule therefore was produced with unreactive terminal methoxy groups which could not readily be further derivatized, and with very short arms, including three ethylene oxide units per arm.

There is a need for the development of methods for the synthesis of monodisperse, well characterized PEO star molecules. There also is a need in many biomedical applications for the development of methods for the synthesis of PEO star molecules with PEO arms of significant length with functionalizable groups which are capable of reacting with one or more additional molecules, such as biologically active molecules.

It is therefore an object of the invention to provide PEO star molecules which are monodisperse. It is a further object of the invention to provide star molecules having as arms PEO chains of significant length. It is a further object of the invention to provide methods for the synthesis of PEO star molecules which include terminal functionalizable groups. It is another object of the invention to provide PEO star molecules with functionalizable groups which are capable of reacting with one or more additional, biologically active molecules such as therapeutic agents or specific binding molecules.

SUMMARY OF THE INVENTION

Methods are provided for the synthesis of poly(ethylene oxide) ("PEO") star macromolecules including functionalizable groups. In one embodiment, a core molecule, such as a dendritic molecule including a plurality of dendritic branches, with terminal reactive groups, is reacted with functionalizable poly(ethylene oxide) ("PEO") molecules. The functionalizable poly(ethylene oxide) molecules include a reactive group capable of reacting with the reactive group on the dendritic molecule, and a functionalizable group capable of being chemically modified, which optionally is protected. In the reaction, the PEO molecules are covalently attached to the termini of the branches on the dendritic molecule, to form a PEO star macromolecule with terminal functionalizable groups. Preferably, the functionalizable PEO is a heterofunctional linear PEO which includes the reactive group at one terminus and the functionalizable group at the other terminus. The functionalizable groups on the PEO molecules then may be deprotected if necessary, and then further derivatized, for example, by the attachment of a biologically active molecule or polymer thereof.

BRIEF DESCRIPTION OF THE DRAWINGS

Please review the following descriptions of the Figures:

FIG. 14 is a table showing the calculated and experimentally determined molecular weights of PEO star macromolecules as a function of PEO type and dendrimer functionality.

DETAILED DESCRIPTION OF THE INVENTION

Glossary of Terms

The following abbreviations are defined so that their use in this application is unambiguous:

| Abbreviation | Definition |
| --- | --- |
| PEO | linear poly(ethylene oxide) |
| PEG | poly(ethylene glycol) |
| STAR PEO | multi-armed molecule, with a compact central core and multiple PEO chains extending from the central core |
| NHS | N-hydroxysuccinimide |
| t-boc | tert-butoxycarbonyl |
| Mw | weight average molecular weight |
| Mn | number average molecular weight |
| pdi | polydispersity index (Mw/Mn) |

Methods for the synthesis of substantially monodisperse and functionalizable poly(ethylene oxide) ("PEO") star macromolecules are provided. The functionalizable PEO star macromolecules advantageously may be readily further derivatized, for example by the attachment of therapeutically active biological molecules, diagnostic agents, targeting agents, or combinations thereof.

Formation of Functionalizable PEO Star Macromolecules

Figures 1, 2:
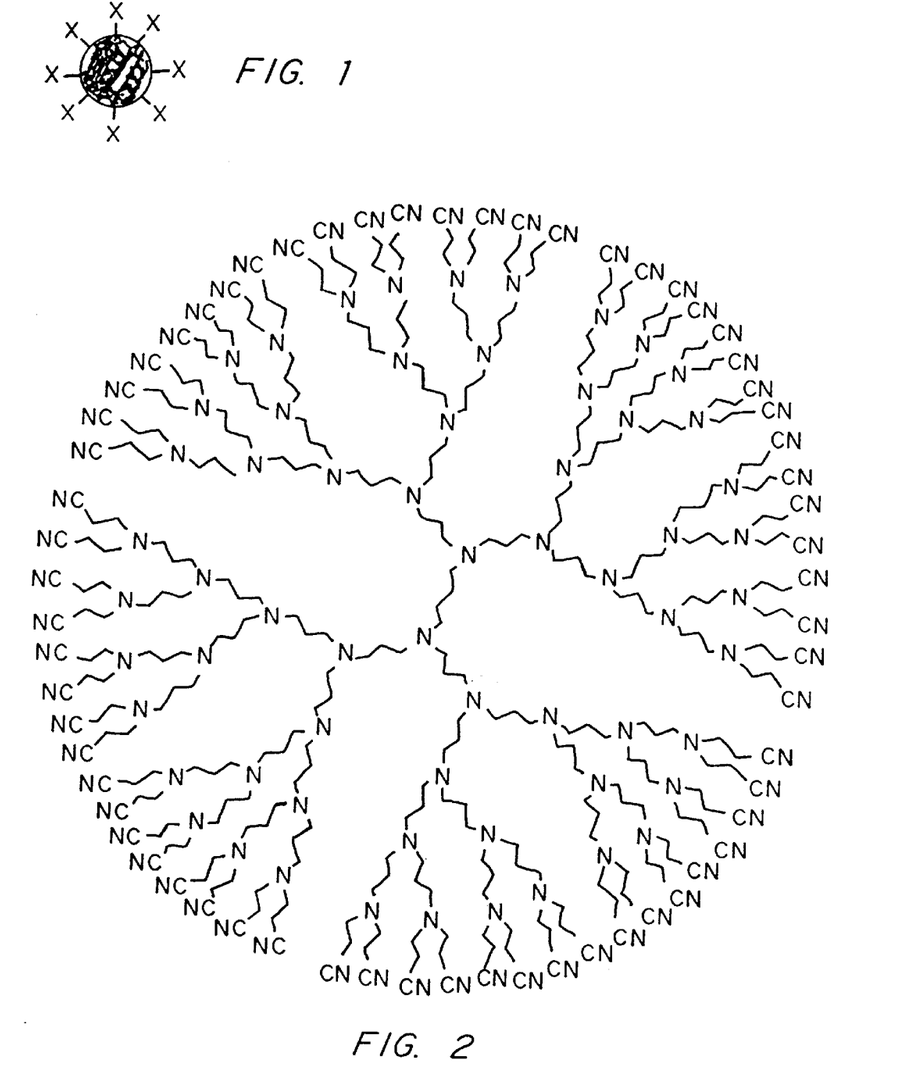
FIG. 1 is an illustration of a core molecule including a plurality of reactive groups, X.
FIG. 2 is an illustration of a dendrimer core molecule including 64 terminal cyano groups.
Figure 3:
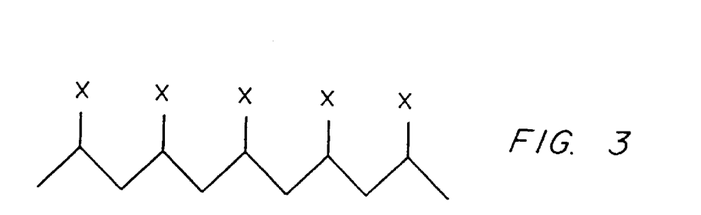
FIG. 3 is an illustration of a comb-like core molecule including a plurality of reactive groups, X.
Figure 4:
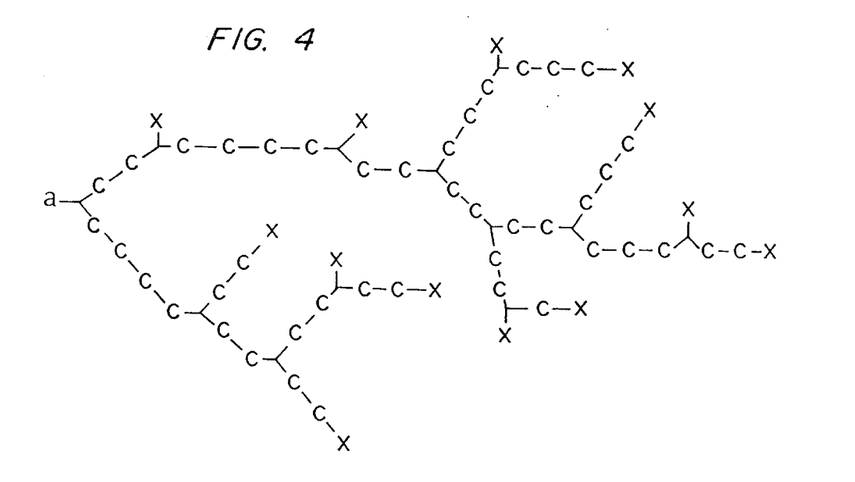
FIG. 4 is an illustration of a hyperbranched core molecule including a plurality of reactive groups, X.

Functionalizable PEO star molecules are synthesized by attachment of heterofunctional PEO chains or "arms" to a core molecule including a plurality of reactive groups which is shown schematically in FIG. 1. For example, the core molecule may be a dendritic branched molecule including reactive groups at the termini of the branches which are capable of reacting with a functional group on the heterofunctional PEO chains. An example of dendritic branched core molecule is shown in FIG. 2. Alternative core molecules include comb-like molecules carrying a reactive side group, X, such as poly(amino styrene), illustrated in FIG. 3, wherein the degree of polymerization may be, for example, in the range of about 10 to 500. In another embodiment, as illustrated in FIG. 4, the core molecule can be a hyperbranched molecule including reactive groups, X, such as amino groups.

In general, the core molecule should be multifunctional. Preferably, the core molecule is compact, in that, in the resulting star macromolecule, the core is the center of the star molecule; the core has a small volume compared with the volume of the star molecule in solution; and the core is effectively shielded by the PEO arms of the star molecule in solution against contact with large biologically active molecules, such as proteins. While the core molecule preferably is compact, it may nonetheless have interior void space capable of holding small molecules, such as described by E. W. Meier et al. (*Polym. Mater. Sci. Eng.*, 73, 123 (1995)), and illustrated in FIG. 2.

To form the PEO star macromolecule, a plurifunctional core molecule, D—(X)$_f$, where f is the number of reactive groups (X), is reacted with PEO chains or "arms" which preferably are in the form a linear molecule, Z—PEO—Y, where the terminal group Y is capable of reacting with —X to form a covalent bond linking the PEO arm to the core. Preferably, the other terminal group Z is inert (for example due to the presence of a protecting group) in that under the conditions of coupling —Y with —X, Z—cannot react with —X. After attachment of the PEO arms to the core to form the PEO star macromolecule, the Z group at the ends of the star molecule may if necessary be transformed, for example by a deprotection step, to a group Z* which is reactive, allowing attachment of bioactive or other molecules, or further extension of arm length by addition of further molecules of Z—PEO—Y.

Suitable reactive groups or protecting groups which can be used in the reaction can be selected and designed using synthetic organic methods available in the art, such as are described in Greene and Wuts, "Protective Groups in Organic Synthesis", Second Edition, John Wiley and Sons, Inc., New York, 1991; and in March, "Advanced Organic Chemistry, Reactions, Mechanisms, and Structure", John Wiley & Sons, New York, 1992, the disclosures of which are incorporated herein.

For example, linear PEO molecules having an N-hydroxysuccinimidyl ester functional group at one end are reacted with a core molecule, such as a dendritic molecule having a predetermined number of primary amine groups. The other end of the PEO molecule includes a terminal functional group capable of being further reacted, but not capable of reacting with the primary amine groups, for example, a hydroxyl or t-boc protected amine group. The reaction produces PEO star macromolecules including a central core attached to the PEO arms via an amide linkage. Depending on the terminal functional group on the linear PEO, the outer ends of the star molecules will be capable of further reaction, after deprotection if necessary. For example, a t-boc protecting group can be removed from a terminal amine group by adding a dilute solution of hydrochloric acid. In this latter case, star molecules terminating with primary amines can be further extended by reacting the terminal amine groups with additional PEO chains or with other molecules.

PEO star macromolecules with a large number of PEO arms, for example, 150 or more arms may be designed and synthesized using this method. The star PEO macromolecules have more end groups than their linear counterparts of equivalent molecular weight, therefore providing a greater number of points of attachment for other molecules, for example, bioactive molecules such as enzymes, peptides, and organic drug molecules or diagnostic or targeting agents, or for attachment to surfaces upon which PEO is to be immobilized. Even using PEO chains of molecular weight measured in thousands (for example, 5,000–10,000), it is possible to attach preformed arms in large number to preformed cores, and to create substantially monodisperse star macromolecules having a low polydispersity index, for example, less than about 1.15.

Core Molecules

The star molecules are synthesized by reaction of heterofunctional PEO chains with a core molecule which is a plurifunctional molecule D—(X)$_f$, where f is the number of reactive groups X per molecule. In one preferred embodiment, the core molecule is a dendrimer including a plurality of dendritic branches with terminal reactive groups. As used herein, the term "dendrimer" refers to a molecule built up from a single starting molecule by sequential covalent reactions with a molecule having reactive sites to produce a branched molecule including terminal reactive groups. An example of the synthesis of a dendrimer is the synthesis of poly(amido-amine) ("PAMAM") Starburst™ dendrimers including terminal amine groups, as described in Tomalia et al., *Macromolecules*, 19 2466 (1986); and U.S. Pat. No. 4,568,737 to Tomalia et al., the disclosures of which are incorporated herein. Each sequential reaction builds the dendrimer up generation by generation, wherein after each reaction, the core has twice the number of active sites (amine groups) on its surface as the generation before. For example, ethylenediamine may be used as the starting material, and reacted in alternate reactions with methyl acrylate and ethylene diamine. One advantage of dendrimers is that they may be synthesized in successive generations to have a precise, known functionality. For example dendrimers may be synthesized with 4, 8, 16, 32, 64, 128, 256, or more primary amine groups. PAMAM dendrimers manufactured by Dendritech, Inc., are available commercially in several generations (sizes) from Aldrich Chemical Company, St. Louis, Mo., as well as from Dendritech, Midland, Mich. These primary amine groups may be used as the point of attachment for the PEO chains to be the "arms" of the star molecule.

Preferably the dendrimer is a dense, branched, spherical molecule, and has between about 8 and 256 reactive groups. FIG. 2 shows a dendrimer which has 64 cyano (CN) groups that can be hydrogenated to become 64 amino groups. In a preferred embodiment, the dendrimer is built up symmetrically generation by generation to produce a symmetrically branched structure including a plurality of terminal reactive groups. However, other possible structures including terminal reactive groups may be used as the core molecule including comb structures, as illustrated in FIG. 3, and hyperbranched molecules, as illustrated in FIG. 4.

In addition to amines, other reactive groups which may be present on the core include carboxylic acids and modified carboxylic acid derivatives such as acid chlorides. Exemplary dendrimers include amine terminated polyamidoamine dendrimers, poly(propylenimine) dendrimers, and polylysine dendrimers.

Dendrimers with reactive terminal groups can be prepared using techniques described, for example, in O'Sullivan, C&EN, pp. 20, Aug. 16, 1993; and Haggin et al., C&EN, pp 26–27, Feb. 6, 1995, the disclosures of which are incorporated herein. Other branched molecules with reactive groups which can be used as the PEO star core include cascade branched globular poly(α,ε-L-Lysine) macromolecules, described in Aharoni et al., *Macromolecules*, 15: 1093–1098 (1982); and in U.S. Pat. No. 4,289,272 to Denkewalter, the disclosures of which are incorporated herein.

Heterofunctional Poly(Ethylene Oxide) Molecules

The PEO star macromolecules preferably are formed by attachment of heterofunctional PEO molecules to the branched core molecule including terminal reactive groups, such as a dendrimer core. As used herein, the term "heterofunctional PEO molecule" refers to PEO molecules, or poly(ethylene glycol) molecules which are preferably linear, and which are provided with different terminal groups at each end of the linear molecule, wherein one terminal group is a reactive group, Y, capable of covalent reaction with the reactive group, X, on the core molecule; and wherein the other terminal group, Z, is a functionalizable group which is capable of being chemically modified, after attachment of the PEO molecules to the core. In a preferred embodiment, the linear heterofunctional PEO molecules include between about 10 to 350 ethylene oxide units per chain.

Figures 5A, 5B, 5C, 5D, 5E:
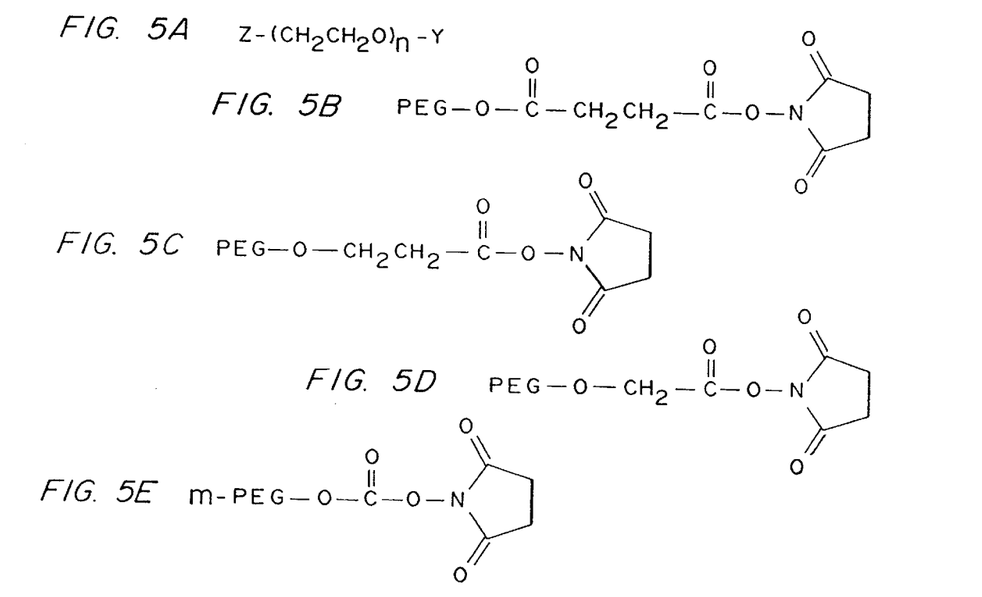
FIG. 5a illustrates the structure of a heterofunctional PEO molecule including reactive group, Y, and functionalizable group, Z.
FIG. 5b illustrates the structure of a linear heterofunctional PEO molecule with a terminal N-succinimidyl succinate group.
FIG. 5c illustrates the structure of a linear heterofunctional PEO molecule with a terminal N-succinimidyl propionate group.
FIG. 5d illustrates the structure of the N-succinimidyl ester of carboxymethylated PEO.
FIG. 5e illustrates the structure of a linear heterofunctional PEO molecule with a terminal N-succinimidyl carbonate group and a terminal methoxy group.

The heterofunctional PEOs are defined in one embodiment, as illustrated in FIG. 5a, as linear molecules having the following formula:

$$Z—(CH_2CH_2O)_n—Y,$$

wherein n is between about 10 and 500, preferably between about 50 to 250;

wherein Y is a reactive group capable of covalent reaction with the reactive group, X, on the core molecule; and Z is a functionalizable group which is capable of being chemically modified after the covalent reaction.

The reactive group Y on the heterofunctional molecule will depend on the reactive group present on the core molecule, and can be, for example, —OH, NH$_2$, carboxylic acid, a modified carboxylic acid such as an ester, an isocyanate or an aldehyde. In the case where the reactive group X on the core molecule is an amine, the reactive group Y can include a functional group capable of forming covalent bonds with a free amine.

Figure 5F:
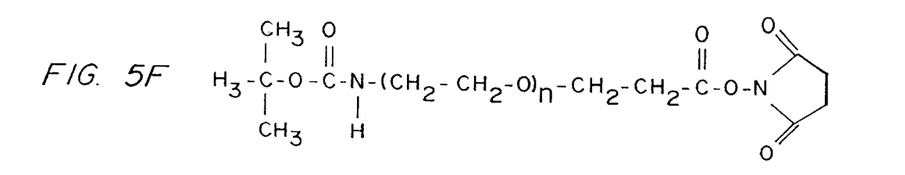
FIG. 5f shows the structure of a linear heterofunctional PEO molecule including a terminal N-succinimidyl propionate group and a terminal t-boc blocked amino group.
Figure 5G:
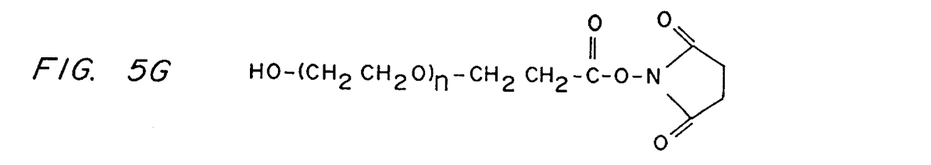
FIG. 5g shows the structure of a linear heterofunctional PEO including a terminal reactive group, N-succinimidyl propionate, and a terminal hydroxyl group.

In one embodiment, the reactive group may be, for example, an N-hydroxy succinimidyl ("NHS") derivative, such as an N-succinimidyl succinate, as illustrated in FIG. 5b; an N-succinimidyl propionate, as illustrated in FIG. 5c; an N-succinimidyl ester of a carboxymethyl group, as illustrated in FIG. 5d; or an N-succinimidyl carbonate, as illustrated in FIG. 5e. The functionalizable group, Z, on the heterofunctional PEO molecule may includes groups such as a hydroxyl or protected hydroxyl group, a carboxyl or a protected carboxyl group, or an amino or protected amino group. FIGS. 5f and 5g illustrate heterofunctional PEO molecules in which the NHS derivative is the N-succinimidyl succinate and the functionalizable end Z is respectively a t-boc blocked amino group and a hydroxyl group.

Figures 6A, 6B:
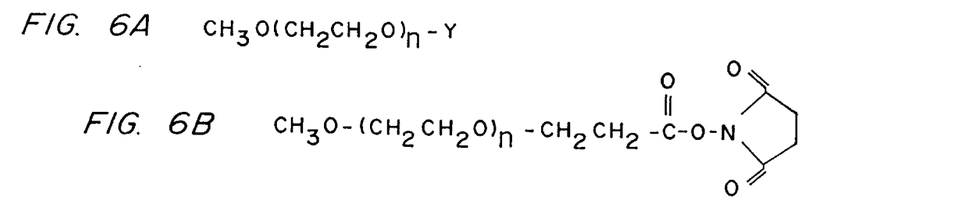
FIG. 6a shows the structure of a linear PEO including a terminal methoxy group and a terminal reactive group, Y.
FIG. 6b shows the structure of a linear PEO molecule including the terminal reactive group, N-succinimidyl propionate, and a terminal methoxy group.

Other heterofunctional PEOs may be designed and synthesized using organic chemistry techniques available in the art, and/or may be obtained commercially. Linear PEOs (which are also referred to as PEGs) with modified end groups are available commercially from Shearwater Polymers, Inc. (Huntsville, Ala.) which have terminal groups including epoxide, hydroxyl, carboxyl, amine, t-Boc protected amine, and various N-hydroxyl succinimidyl esters. FIGS. 6a and 6b illustrate linear PEO molecules provided with a terminal methoxy group and a terminal reactive group, Y and N-succinimidyl proprionate, respectively.

Derivitization of the Star Macromolecules

Figure 7:
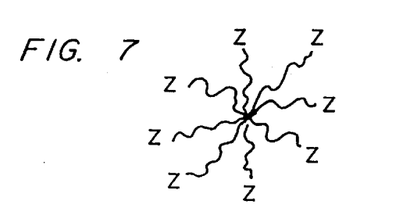
FIG. 7 is an illustration of a PEO star macromolecule including eight PEO arms provided with a terminal functionalizable group, Z.

The PEO star macromolecules in one embodiment, as illustrated schematically in FIG. 7, include plural PEO chains provided with a terminal functionalizable group, Z. The PEO chains in the star molecule may be derivatized, for example, by attachment of a biomolecule or polymer thereof to free hydroxyl or other functionalizable group, Z, at the termini of the PEO chains. Preferred functionalizable groups Z on the PEO chains are protected —NH$_2$ and —OH. Biologically active molecules, such as antibodies, enzymes, growth factors, or diagnostic agents may be attached to the PEO star molecules, after the functionalizable group Z has become active by deprotection, or directly (e.g. Z=—OH). Alternatively, two or more different molecules may be attached to the star molecule.

Any of a range of biological molecules, such as nucleic acids, amino acids, saccharides or polymers thereof may be attached to the terminal reactive groups on the PEO chains of the star molecules. As used herein, the term "nucleic acids, amino acids and saccharides, or polymers" includes natural and synthetic derivatives thereof. Exemplary biological molecules include proteins such enzymes, antibodies and cell recognition molecules. Other exemplary molecules include cell adhesion molecules, growth factors, metals, lipids, and polysaccharides, as well as organic drug molecules. As used herein, the term "protein" is defined as a polymer of two or more amino acids or amino acid derivatives, such as a peptide, polypeptide or enzyme. The biological molecule attached to the PEO star molecule also may be a specific binding molecule, such as a monoclonal antibody or fragment thereof, or equivalent thereof. The biological molecule also may be a member of a specific binding pair such as antigen/antibody or ligand/receptor.

Figure 8:
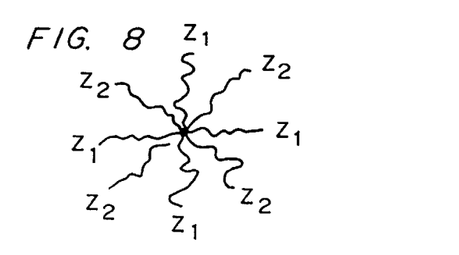
FIG. 8 is an illustration of a PEO star macromolecule provided with PEO arms which include two types of terminal functionalizable groups, $Z_1$ and $Z_2$.

In a further embodiment, at least two different biological molecules or polymers thereof may be covalently attached to the functionalizable groups on the PEO chains, to produce a multifunctional star molecule. For example, two different enzymes, or an enzyme and a polysaccharide may be attached to the PEO star molecule. In one embodiment, two different functionalizable groups, $Z_1$ and $Z_2$, may be provided on the PEO star macromolecule for further reaction, as illustrated in FIG. 8.

Figure 9:
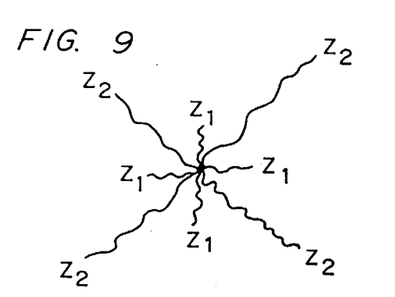
FIG. 9 is an illustration of a PEO star macromolecule including PEO arms of two different lengths, wherein the shorter arms include the terminal group $Z_1$, and the longer arms include terminal group $Z_2$.
Figure 10:
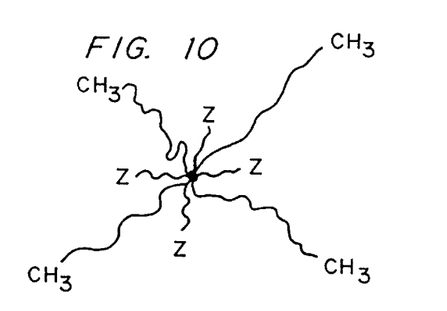
FIG. 10 is an illustration of a PEO star macromolecule including longer PEO arms terminated by an inert methyl group, and shorter PEO arms terminated by a functionalizable group, Z.

In a further embodiment, illustrated in FIG. 9, the heterofunctional PEO molecules are provided in the reaction in two or more different length fractions, ranging, for example, from about 10 to 350 ethylene oxide units, wherein the fractions of different lengths have a narrow MW distribution, and may include the same or different functionalizable groups or reactive groups. The PEO molecules of different lengths and functionalizable groups may be reacted with the dendrimer to produce a PEO star macromolecule with a preselected distribution of PEOs of selected lengths and a selected distribution of terminal functionalizable groups. If desired, nonfunctionalizable PEO molecules, including nonreactive groups such as terminal methyl groups, also may be incorporated into the PEO star macromolecule, as illustrated in FIG. 10.

Figure 11:
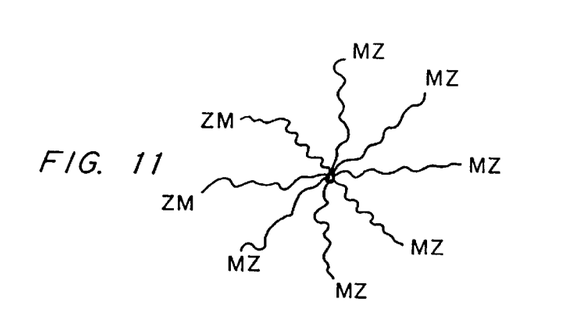
FIG. 11 is an illustration of a PEO star macromolecule including plural PEO arms terminating in a hydrolysable moiety, M, linked to a functionalizable group, Z.

In a further embodiment, as illustrated in FIG. 11, the functionalizable groups, Z, on the linear heterofunctional PEO molecules may be linked to a hydrolyzable moiety, M, either before or after formation of the PEO star molecule, and the hydrolyzable moiety further may be linked to a biologically active molecule. Exemplary hydrolyzable groups include lactic acid, glycolic acid, poly(lactic acid), poly(glycolic acid), poly(lactic-co-glycolic acid), and polyanhydrides. PEO star molecules useful in drug delivery applications may be fabricated with a proportion of shorter PEO chains attached via the functionalizable group to a hydrolyzable moiety linked to a biologically active molecule, and a proportion of longer PEO molecules on the star molecule attached to a cell recognition molecule.

Hydroxyl termini of PEO chains on the star molecules can be activated and then a ligand, such as an antibody, may be attached to the termini, as described in U.S. Pat. Nos. 5,171,264 and 5,275,838, the disclosures of which are incorporated herein by reference. For example, the free hydroxyl groups can be activated with tresyl chloride and then reacted with a ligand that contains a free amino acid or thiol group to form a covalent linkage with the ligand. Harris, *J. Macromolecular Sci. Reviews in Macro. Chem. Phys.*, C25(3):325–373 (1985).

The present invention will be further understood by reference to the following non-limiting examples, in which the following materials and equipment were used.

Equipment and Materials

Analysis of all samples was done using gel permeation chromatography (GPC), in series with refractive index (RI) and light scattering (LS) measurements. Determination of the molecular weight distribution and polydispersity of all samples was made using gel permeation chromatography (GPC) in conjunction with light scattering (LS). The GPC used was a Waters Model 150C containing two Tosohaas TSK-gel columns in series, G6000PW and G4000PW. The GPC eluate from the columns pass through a Wyatt Dawn Model F laser photometer and then through the refractive index detector contained within the Model 150C system. Voltage measurements taken from the detectors are recorded every second and converted to light intensity and refractive index measurements respectively. The differential refractive index increment for the PEO stars is assumed to be equal to that of linear PEO, since the weight fraction of PEO is greater than 0.95. All calculations were made through ASTRA, a software package designed for use with the Wyatt Dawn Model F, which is run on a CUI 386 PC. Polydispersity is measured as Mw/Mn, with a polydispersity index (pdi) of 1.15 or less taken as indicating that the sample is substantially monodisperse.

The heterofunctional linear PEO molecules were obtained from Shearwater Polymers, Inc., Huntsville, Ala. The dendrimers used as cores of the PEO star molecules were PAMAM Starburst™ dendrimers provided and synthesized by Dendritech, and are synthesized as described in Tomalia et al., *Macromolecules*, 19:2466 (1986), with the exception that ethylene diamine was used as the starting molecule instead of ammonia, followed by alternate reactions with methyl acrylate and ethylene diamine. These dendrimers were synthesized in successive generations to have 16, 32, 64, 128, or 256 primary amine groups.

EXAMPLE 1

Reaction of Dendrimers with Heterofunctional Poly (Ethylene Glycol) Molecules

Different PEO star macromolecules were synthesized by the reaction of PAMAM dendrimers with 16, 32, 64, 128, or 256 primary amine groups with the heterofunctional PEO molecules, MeO—PEO—$CH_2CH_2$CONHS (MW 5000), HO—PEO—$CH_2CH_2$CONHS (MW 4000), and tboc-HN—PEO—$CH_2CH_2$CONHS (MW 3400). The molecular weights of the heterofunctional PEO molecules are those reported by the manufacturer.

Reaction of Dendrimers with Heterofunctional PEO Molecules.

A known quantity of dendrimer was dissolved in 0.1M sodium bicarbonate buffer. It was assumed that one heterofunctional PEO molecule would react with each primary amine group on the dendrimer's surface. Based on this assumption the dendrimer solution was then added to a 1.6× molar excess of heterofunctional PEO. The dendrimer was added to the buffer before dissolving the heterofunctional PEO in buffer, due to the high rate of hydrolysis of the NHS group and the desire to avoid contact of the PEO with water until the dendrimer was present. The solution was then stirred for 2 hours to permit attachment of the PEO molecules to the dendrimer to form star PEO arms covalently linked to the dendrimer.

Terminal t-boc protecting groups on the PEO star molecule if present were removed by treatment with dilute hydrochloric acid and stirring overnight. This yielded a PEO star molecule with free terminal amino groups, capable of binding or reacting with further molecules.

Separation of Unreacted Heterofunctional Poly(Ethylene Oxide)

The PEO star macromolecules prepared in the above manner contained excess unreacted linear heterofunctional PEO. This PEO was removed via ultrafiltration using a stirred ultrafiltration cell (Amicon Corp., Beverly, Mass). The membranes used depended on the size of the star synthesized. For example, a star synthesized by reacting a dendrimer containing 64 amine groups with methoxy PEO (MW=5000), is completely retained by an Amicon YM100 (100,000 molecular weight cutoff (MWCO), regenerated cellulose) membrane. Therefore this membrane was used to separate these stars from the methoxy PEO. However, a star prepared using a dendrimer containing only 16 amino groups would pass through a YM100 membrane. Therefore a YM30 (30,000 MWCO, regenerated cellulose) membrane was used to separate this star from linear PEO. The presence of unreacted PEO remaining in solution was monitored by injecting a sample of both the permeate (solution passing through the membrane) and the retentate (solution retained by the membrane) into the GPC/LS. Stars diafiltered into ion free water from buffer solution were then filtered using a 0.5 micron filter and the water was lyophilized off.

Synthesis of PEO Star Molecules by Reaction of PAMAM Dendrimers with MeO—PEO—$CH_2CH_2CONHS$, HO—PEO—$CH_2CH_2CONHS$, and t-Boc-PEO—$CH_2CH_2CONHS$ Eleven different types of star molecules were synthesized. Three types of heterofunctional PEO molecules, i) MeO—PEO—$CH_2CH_2CONHS$ (MW 5000), shown in FIG. 6b; ii) HO—PEO—$CH_2CH_2CONHS$ (MW 4000), shown in FIG. 5g; and iii) t-Boc-PEO—$CH_2CH_2CONHS$, shown in FIG. 5f, were reacted with PAMAM dendrimers of generation 2–6, having functionalities ranging from 16 to 256.

Figure 12:
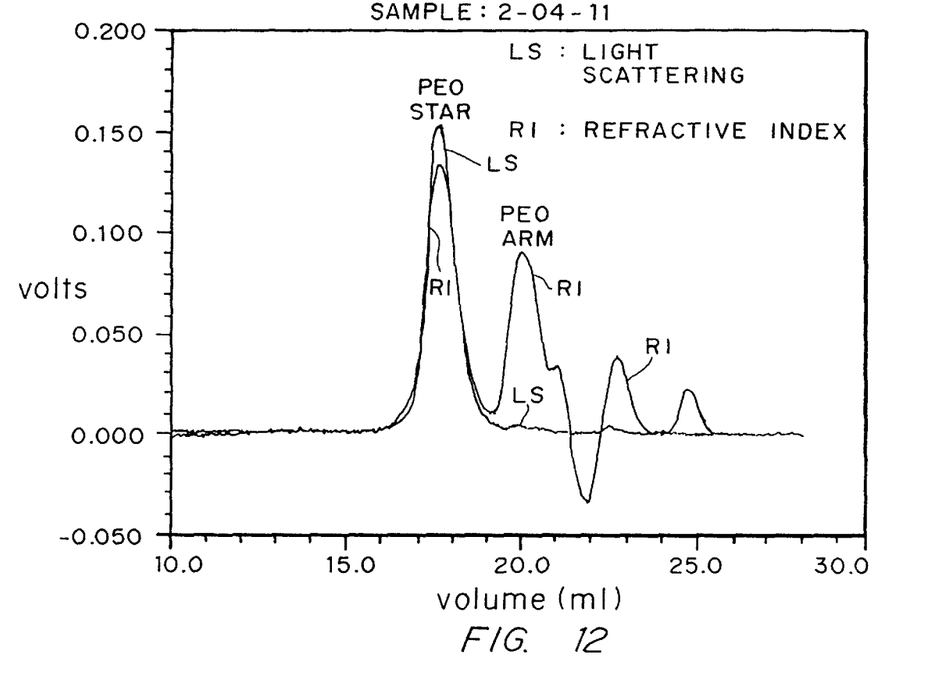
FIG. 12 is a gel permeation chromatography ("GPC") chromatogram showing light scattering and refractive index signals versus elution volume of the product of the reaction of a generation 4 poly(amidoamine) ("PAMAM") dendrimer with MEO—PEO—CH$_2$CH$_2$CONHS.

A sample GPC chromatogram taken after reacting a generation 4 dendrimer containing 64 primary amine groups with MeO—PEO—$CH_2CH_2CONHS$ is shown in FIG. 12. The first peak shows the star molecule produced. The second peak is unreacted linear PEO, while the last peaks are due to salt. The narrowness of the first peak and the near overlap of the refractive index trace with the light scattering trace indicate that a nearly monodisperse sample was produced. The number average molecular weights ($M_n$), polydispersity indexes (pdi—weight divided by number average molecular weight) and functionalities for the star macromolecules are summarized in Table 1 in FIG. 14. These results show that when reacted with dendrimers of low functionality (<32), the heterofunctional PEOs react with substantially all the amine groups to create a relatively monodisperse molecule. However, as the functionality gets to be greater than 32, steric hindrances preclude all the PEOs from being able to react with all the amine groups on the dendrimers and $M_n$ is less than expected, although star molecules are produced with up to 140 arms. Advantageously, even when not all the amine groups on the dendrimer are reacted with PEO, a nearly monodisperse sample of star molecules still results.

Figure 13:
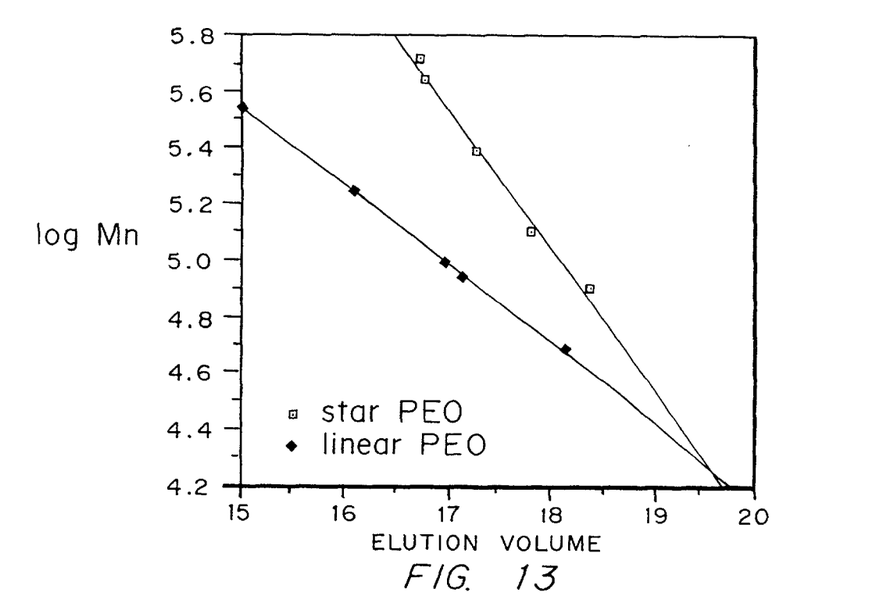
FIG. 13 is a graph showing the logarithm of molecular weight (Mn) as a function of elution volume obtained from GPC of linear PEO and PEO star molecules, of which the PEO arm molecular weight was 5000.

FIG. 13 shows a plot of log Mn as function of elution volume for linear PEO molecules and PEO star molecules formed from HO—PEO—$CH_2CH_2CONHS$ of 5000 molecular weight. At the same elution volume, the star molecule has a much higher molecular weight than the linear PEO molecule. For example, the Mn of the star molecule prepared from HO—PEO—$CH_2CH_2CONHS$ eluting at 7 ml is 324,000. The molecular weight of the linear PEO eluting at the same volume is only 94,000, thus confirming that a PEO star molecule has a considerably smaller hydrodynamic volume than a linear PEO molecule of equal molecular weight.

EXAMPLE 2

Synthesis of PEO Star Molecules by Reaction of Dendrimers with a Heterofunctional PEO including a Protected Amine Group Using the general procedure described above, a generation 2 PAMAM dendrimer, with an amine functionality ("f") of 16 was reacted with the heterofunctional PEO, tboc-HN—PEO—$CH_2CH_2CONHS$ of MW 3400. GPC/LS analysis indicated that the product PEO star molecule had a Mn of 88,100, and a pdi of 1.06. The same reaction using the generation 3 (f=32) dendrimer by GPC/LS analysis produced a PEO star molecule with a Mn of 173,000, and a pdi of 1.09. Reaction of the heterofunctional PEO with the generation 4 dendrimer (f=64) from GPC/LS analysis had a Mn of 239,000, and a pdi of 1.03.

EXAMPLE 3

Preparation of PEO Star Molecules with Extended PEO Arms

PEO star molecules with extended PEO arms may be synthesized using the methods described in Example 1. In some applications, it is desired to have long PEO arms on the star molecule. However, as the length of the arms increases, steric hindrance may prevent the reaction from reaching completion. To avoid this problem, a series of shorter chain PEO chains are sequentially reacted with the dendrimer, wherein the shorter chains include a terminal first group capable of reacting with free amines, and a second terminal protected amine group. After attachment of the shorter PEO chains and deprotection of the amino group, the PEO can again be reacted with the star molecule, and the process can be repeated to grow PEO arms of a desired length.

In one example, eight microliters of generation 3 PAMAM dendrimer was charged to 0.4 ml sodium bicarbonate buffer. This solution then was added to 33.8 mg of a heterofunctional linear PEO, tboc-HN—PEO—$CH_2CH_2CONHS$ (3400 MW). Another 0.1 ml of buffer was used to rinse out the vial. After letting the reaction proceed overnight under constant stirring, a sample was taken for GPC/LS analysis, from which Mn was determined to be 159,000, and the polydispersity index ("pdi") was found to be 1.16. The remainder of the solution was brought to 0.5N HCl, and left stirring overnight. The reaction mixture then was diafiltered into 0.1M $NaHCO_3$ solution using an Amicon YM 100 membrane, thereby removing unreacted PEO. 44.5 mg of the linear PEO then was charged to the reaction mixture which was left stirring for 3 hours. Another sample was taken for GPC/LS analysis, and the remainder of the solution was again brought to 0.5N HCl. The Mn of this sample was found to be 326,000, and the pdi was found to be 1.13. The diafiltration process was repeated, and 36.6 mg of the linear PEO was added, and the reaction was allowed to proceed for three hours with constant stirring. GPC/LS analysis showed that the Mn was 588,000, and the pdi was 1.11.

Modifications and variations of the present invention will be obvious to those skilled in the art from the foregoing detailed description. Such modifications and variations are intended to come within the scope of the following claims.

We claim:

1. A method for synthesizing a star macromolecule containing poly(ethylene oxide) moeities that contain a terminal reactive group, comprising:
   i) providing a compact core molecule comprising a plurality of first reactive groups;
   ii) providing linear heterofunctional poly(ethylene oxide) ("PEO") molecules, wherein each PEO molecule comprises:
      first and second termini;
      a second reactive group at the first terminus capable of reacting with the first reactive groups on the core molecule; and
      a third reactive group at the second terminus which is not capable of reacting with the first reactive groups on the core molecule; and
   iii) reacting the first reactive groups on the core molecule with the second reactive groups on the PEO molecules to covalently attach the PEO molecules to the core molecule.

2. The method of claim 1 wherein the core molecule has a structure selected from the group consisting of a hyperbranched structure and a comb structure.

3. The method of claim 1 wherein the core molecule is a dendritic molecule including a plurality of dendritic branches comprising a first reactive group at the terminus thereof.

4. The method of claim 3 wherein the dendritic molecule is selected from the group consisting of an amine terminated polyamidoamine dendrimer, a poly(propylenimine) dendrimer, and a polylysine dendrimer.

5. The method of claim 1 wherein the PEO star macromolecule is substantially monodisperse.

6. The method of claim 3 wherein the dendritic molecule comprises between about 8 and 256 reactive groups.

7. The method of claim 1 wherein the first reactive group is an amine.

8. The method of claim 1 wherein the first reactive group is selected from the group consisting of a carboxylic acid and a modified carboxylic acid, the second reactive group on the PEO molecule is an amino group, and the third reactive group on the PEO molecule is selected from the group consisting of a protected hydroxyl group, a protected amino group, and a protected carboxyl group.

9. The method of claim 1 wherein the second reactive group on the PEO molecule is selected from the group consisting of a carboxylic acid, a modified carboxylic acid, an isocyanate and an aldehyde.

10. The method of claim 7 wherein the second reactive group on the PEO molecule is an N-hydroxysuccinimidyl ester of a carboxylic acid and the third reactive group is a hydroxyl group.

11. The method of claim 1 wherein the third reactive group is selected from the group consisting of amino, protected amino, hydroxyl, protected hydroxyl, carboxyl and protected carboxyl.

12. The method of claim 1 wherein the PEO molecules provided in step ii) have a length of about 10 to 350 ethylene oxide units.

13. The method of claim 1 wherein the third reactive groups on the PEO molecules provided in step ii) are protected, and wherein the method further comprises deprotecting the third reactive groups after step iii).

14. The method of claim 13 further comprising covalently attaching the third reactive groups on the PEO molecules to a biologically active molecule or polymer thereof.

15. The method of claim 14 wherein the biologically active molecule is selected from the group consisting of an amino acid, a peptide, a protein, a nucleic acid, a lipid, an organic drug, a saccharide and a polysaccharide.

16. The method of claim 14 wherein the biologically active molecule is selected from the group consisting of a cell adhesion molecule, a growth factor, and a metal.

17. The method of claim 14 wherein the biologically active molecule is a specific binding molecule.

18. The method of claim 13 further comprising covalently attaching at least two different molecules or polymers thereof to the third reactive groups on the PEO chains on the star macromolecule.

19. The method of claim 1 wherein the heterofunctional PEO molecules provided in step ii) comprise a mixture of different lengths ranging from between about 10 and 350 ethylene oxide units.

20. The method of claim 19 wherein the PEO molecules comprise first and second fractions of different lengths and of narrow molecular weight distribution.

21. The method of claim 20 wherein the PEO molecules in the first and second fractions comprise different third reactive groups; and
   wherein the PEO molecules in the first and second fractions comprise the same second reactive group.

22. The method of claim 20 further comprising, after step iii), reacting the third reactive groups on one of the PEO fractions on the PEO star macromolecule with linear PEO molecules comprising a fourth reactive group.

23. The method of claim 1 further comprising providing in step ii) PEO molecules that do not contain a third reactive group and which have a length greater than the heterofunctional PEO molecules and have the same second reactive group as the heterofunctional PEO molecules, to incorporate PEO molecules that do not contain a third reactive group into the star macromolecule.

24. The method of claim 23 further comprising, after step iii), attaching the third reactive group on the PEO star macromolecules to a biologically active molecule.

25. The method of claim 1 further comprising linking the third reactive groups on the PEO star macromolecules to a hydrolyzable moiety.

26. The method of claim 25 further comprising linking the hydrolyzable moiety to a biologically active molecule.

27. The method of claim 26 wherein the hydrolyzable moiety is selected from the group consisting of lactic acid, glycolic acid, poly(lactic acid), poly(glycolic acid), poly (lactic-co-glycolic acid), and polyanhydride.

28. The method of claim 20 further comprising linking the third reactive groups on the fraction of longer PEO molecules on the star molecule to a cell recognition molecule, and linking the fraction of shorter PEO molecules to a hydrolyzable moiety linked to a biologically active molecule.

29. A star macromolecule formed by:
   i) providing a compact core molecule comprising a plurality of first reactive groups;
   ii) providing linear heterofunctional poly(ethylene oxide) ("PEO") molecules, wherein each PEO molecule comprises:
      first and second termini;
      a second reactive group at the first terminus capable of reacting with the first reactive groups on the core molecule; and
      a third reactive group at the second terminus; and
   iii) reacting the first reactive groups on the core molecule with the second reactive groups on the PEO molecules to covalently attach the PEO molecules to the core molecule.

30. The star macromolecule of claim 29 wherein the core molecule has a structure selected from the group consisting of a hyperbranched structure and a comb structure.

31. The star macromolecule of claim 29 wherein the core molecule is a dendritic molecule including a plurality of dendritic branches comprising a first reactive group at the terminus thereof.

32. The star macromolecule of claim 29 wherein the PEO star macromolecule is substantially monodisperse.

33. The star macromolecule of claim 31 wherein the dendritic molecule is selected from the group consisting of an amine terminated polyamidoamine dendrimer, a poly (propyleneimine) dendrimer, and a polylysine dendrimer.

34. The star macromolecule of claim 31 wherein the dendritic molecule comprises between about 8 and 256 reactive groups, and wherein the PEO molecules have a length of between about 10 and 350 ethylene oxide units.

35. The star macromolecule of claim 29 further comprising at least one biologically active molecule or polymer thereof covalently attached to the third reactive groups on the PEO molecules.

36. The star macromolecule of claim 35 wherein the biologically active molecule is selected from the group consisting of an amino acid, a peptide, a protein, a nucleic acid, a lipid, an organic drug, a saccharide and a polysaccharide.

37. The star macromolecule of claim 29 wherein the heterofunctional PEO molecules provided in step ii) comprise first and second fractions of different lengths and of narrow molecular weight distribution, and include between about 10 and 350 ethylene oxide units.

38. The star macromolecule of claim 37 wherein the PEO molecules in the first and second fractions comprise different third reactive groups.

39. The star macromolecule of claim 37 further comprising a cell recognition molecule linked to the third reactive group on the fraction of longer PEO molecules on the star macromolecule, and a biologically active molecule linked to a hydrolyzable moiety linked to the fraction of shorter PEO molecules on the star macromolecule.

40. A poly(ethylene) oxide ("PEO") star macromolecule formed by i) providing a compact core molecule including a plurality of accessible first reactive groups;

ii) providing a mixture of linear heterofunctional and monofunctional PEO molecules, wherein the PEO molecules comprise a second reactive group capable of reacting with the first reactive group on the core, and wherein the linear heterofunctional PEO molecules comprise first and second termini wherein the second reactive group is on the first terminus and a third reactive group is present on the second terminus, and iii) reacting the first reactive groups on the core molecule with the second reactive groups on the PEO molecules to covalently attach the PEO molecules to the core molecule.

41. The star macromolecule of claim 40 wherein the monofunctional PEO molecules have a substantially different degree of polymerization than the heterofunctional PEO molecules.

42. The star macromolecule of claim 40 further comprising a biologically active molecule attached to the third reactive group on the PEO star macromolecule.

* * * * *